US008865460B2

(12) United States Patent
Orr et al.

(10) Patent No.: US 8,865,460 B2
(45) Date of Patent: Oct. 21, 2014

(54) CO-CULTURE BIOREACTOR SYSTEM

(75) Inventors: David E. Orr, Lafayette, IN (US);
Karen J. L. Burg, Clemson, SC (US)

(73) Assignee: Clemson University Research Foundation, Clemson, SC (US)

( * ) Notice: Subject to any disclaimer, the term of this patent is extended or adjusted under 35 U.S.C. 154(b) by 1069 days.

(21) Appl. No.: 11/996,610

(22) PCT Filed: Aug. 11, 2006

(86) PCT No.: PCT/US2006/031354
§ 371 (c)(1),
(2), (4) Date: Jul. 23, 2008

(87) PCT Pub. No.: WO2007/021919
PCT Pub. Date: Feb. 22, 2007

(65) Prior Publication Data
US 2008/0293135 A1 Nov. 27, 2008

Related U.S. Application Data

(60) Provisional application No. 60/707,753, filed on Aug. 12, 2005.

(51) Int. Cl.
*C12M 3/00* (2006.01)
*C12M 1/00* (2006.01)
*C12M 1/42* (2006.01)
*C12M 1/12* (2006.01)

(52) U.S. Cl.
CPC ............... *C12M 25/14* (2013.01); *C12M 29/04* (2013.01); *C12M 23/34* (2013.01); *C12M 35/08* (2013.01)
USPC .................. 435/305.2; 435/289.1; 435/299.1; 435/305.1; 435/357; 435/297.2

(58) Field of Classification Search
CPC ...... C12M 23/04; C12M 23/34; C12M 23/42; C12M 23/44; C12M 23/58; C12M 25/14
USPC ............. 435/289.1, 299.1, 305.1, 305.2, 357, 435/297.2
See application file for complete search history.

(56) References Cited

U.S. PATENT DOCUMENTS 5,153,132 A 10/1992 Goodwin et al.
5,160,490 A 11/1992 Naughton et al.
(Continued)

FOREIGN PATENT DOCUMENTS

DE 1957774 A1 5/1996
EP 0700990 A2 3/1996
(Continued)

OTHER PUBLICATIONS
Presentation entitled "A Novel Bioreactor Design for Cell Growth on Discrete Tissue Engineering Constructs" by David E. Orr and Karen J.L. Burg, May 3, 2003 on behalf of Clemson University Department of Bioengineering Tissue Engineering Laboratory.
(Continued)

*Primary Examiner* — Nathan Bowers
(74) *Attorney, Agent, or Firm* — F. Brent Nix; Johnson, Marcou & Isaacs, LLC

(57) ABSTRACT

Disclosed are multi-chambered cell co-culture systems. The systems can be utilized to encourage the growth and development of isolated cells in a dynamic three-dimensional in vitro environment. The cell chambers (10) of the system can be in biochemical communication with adjacent chambers containing cells of different types, but the different cell types are maintained physically separated from one another. In addition, the local environment of each cell chamber can be independently controlled. For example, fluid flow characteristics through a single cell chamber can be independently controlled and maintained for each separate chamber of the system.

29 Claims, 11 Drawing Sheets

(56) References Cited

U.S. PATENT DOCUMENTS

| | | | |
|---|---|---|---|
| 5,190,878 A * | 3/1993 | Wilhelm | 435/297.2 |
| 5,342,313 A | 8/1994 | Campbell et al. | |
| 5,424,209 A | 6/1995 | Kearney | |
| 5,437,998 A | 8/1995 | Schwarz et al. | |
| 5,443,950 A | 8/1995 | Naughton et al. | |
| 5,449,617 A | 9/1995 | Falkenberg et al. | |
| 5,527,705 A | 6/1996 | Mussi et al. | |
| 5,595,909 A | 1/1997 | Hu et al. | |
| 5,605,835 A | 2/1997 | Hu et al. | |
| 5,627,021 A | 5/1997 | Goodwin et al. | |
| 5,658,797 A | 8/1997 | Bader | |
| 5,728,581 A | 3/1998 | Schwartz et al. | |
| 5,763,275 A | 6/1998 | Nagels et al. | |
| 5,785,964 A | 7/1998 | Naughton et al. | |
| 5,849,588 A | 12/1998 | Naughton et al. | |
| 5,858,721 A | 1/1999 | Naughton et al. | |
| 6,001,643 A | 12/1999 | Spaulding | |
| 6,008,049 A | 12/1999 | Naughton et al. | |
| 6,080,581 A | 6/2000 | Anderson et al. | |
| 6,114,164 A | 9/2000 | Dennis et al. | |
| 6,210,959 B1 | 4/2001 | Lodri et al. | |
| 6,218,182 B1 | 4/2001 | Naughton et al. | |
| 6,221,663 B1 | 4/2001 | Bhatia et al. | |
| 6,228,607 B1 | 5/2001 | Kersten et al. | |
| 6,303,375 B1 | 10/2001 | Kimura et al. | |
| 6,372,495 B1 | 4/2002 | Flendrig | |
| 6,379,956 B1 | 4/2002 | Bader | |
| 6,420,110 B1 | 7/2002 | Gyuris et al. | |
| 6,472,200 B1 | 10/2002 | Mitrani | |
| 6,562,616 B1 | 5/2003 | Toner et al. | |
| 6,607,910 B1 | 8/2003 | Dimitrijevich et al. | |
| 6,653,124 B1 | 11/2003 | Freeman | |
| 6,670,173 B1 | 12/2003 | Schels et al. | |
| 6,699,716 B2 | 3/2004 | Sullivan et al. | |
| 6,734,000 B2 | 5/2004 | Chin et al. | |
| 6,759,245 B1 | 7/2004 | Toner et al. | |
| 6,773,458 B1 | 8/2004 | Brauker et al. | |
| 6,803,037 B2 | 10/2004 | Abatangelo et al. | |
| 6,814,547 B2 | 11/2004 | Childers et al. | |
| 6,844,187 B1 | 1/2005 | Wechsler et al. | |
| 6,960,427 B2 | 11/2005 | Haverich et al. | |
| 6,991,652 B2 | 1/2006 | Burg | |
| 7,122,371 B1 | 10/2006 | Ma | |
| 7,435,587 B2 * | 10/2008 | Diresta et al. | 435/325 |
| 7,442,538 B2 * | 10/2008 | Bragos Bardia et al. | 435/243 |
| 2002/0106786 A1 | 8/2002 | Carvalho et al. | |
| 2002/0164780 A1 | 11/2002 | Yao et al. | |
| 2002/0173033 A1 | 11/2002 | Hammerick et al. | |
| 2004/0029264 A1 | 2/2004 | Robbins, Jr. | |
| 2004/0043481 A1 | 3/2004 | Wilson | |
| 2004/0096943 A1 | 5/2004 | Marx et al. | |
| 2004/0132175 A1 | 7/2004 | Vetillard et al. | |
| 2005/0009179 A1 * | 1/2005 | Gemmiti et al. | 435/420 |
| 2005/0158845 A1 | 7/2005 | Wikswo et al. | |

FOREIGN PATENT DOCUMENTS

| | | |
|---|---|---|
| EP | 0700990 A3 | 3/1996 |
| WO | WO 2004/020341 A2 | 3/2002 |
| WO | WO 2004076608 A2 | 9/2004 |
| WO | WO 2004076608 A3 | 9/2004 |
| WO | WO 2004/111209 A1 | 12/2004 |

OTHER PUBLICATIONS

Article—Francesc Godia and Martin Fussenegger; "Membrane-Separated Cocultivation of Cord Blood Hematopoietic Stem Cells and Stromal Cell Lines"; pp. 269-271; Apr. 7, 2006; Animal Cell Technology Meets Genomics.

Article—Jared W. Allen, Salman R. Khetani and Sangeeta N. Bhatia; "In Vitro Zonation and Toxicity in a Hepatocyte Bioreactor"; pp. 110-119; Dec. 8, 2004; Toxicological Sciences 84.

Article—McCulloch AD, Harris AB, Sarraf CE, Eastwood M.; "New Multi-Cue4 Bioreactor for Tissue Engineering of Tubular Cardiovascular Samples Under Physiological Conditions"; pp. 565-573; Mar.-Apr. 2004; Tissue Eng.

Article—S.N. Bhatia, U.IJ. Balis, M.L. Yarmush and M. Toner; "Effect of Cell-Cell Interactions in Preservation of Cellular Phenotype:.Concultivation of Hepatocytes and Nonparenchymal Cells"; pagea 1883-1900; Nov. 1999; The FASEB Journal.

Article—"Qick Guide for Antibody Production Using BD Cell MAb Medium in a CELLine Device"; pp. 1-8; BD Biosciences.

Article—L. L. Licato, V.G. Prieto and E.A. Grimm; "A Novel Preclinical Model of Human Malignant Melanoma Utilizing Bioreactor Rotating-Wall Vessels"; pp. 121-126; Mar. 2001; In Vetro Cell Dev. Biol.—Animal 37.

Article—W.T. Godbey, B.S. Stacey Hindy, Matthew E. Sherman, Anthony Atala; "A Novel Use of Centrifugal Force for Cell Seeding into Porous Scaffolds"; pp. 2799-2805; Sep. 15, 2003; Biomaterials.

Attachment—Citation of Patent Applications.

* cited by examiner

CO-CULTURE BIOREACTOR SYSTEM

RELATED APPLICATIONS

This application claims priority to U.S. Provisional Application Ser. No. 60/707,753, which was filed on Aug. 12, 2005.

This invention was made with government support under PECASE BES 0093805 awarded by the National Science Foundation. The Government has certain rights in the invention.

BACKGROUND OF THE INVENTION

The ability to culture in vitro viable three-dimensional cellular constructs that mimic natural tissue has proven very challenging. One of the most difficult of the many problems faced by researchers is that there are multiple dynamic biochemical interactions that take place between and among cells in vivo, many of which have yet to be fully understood, and yet the complicated in vivo system must be accurately modeled if successful development of engineered tissues in vitro is to be accomplished. The ideal in vitro system should accurately model the mechanical environment as well as the essential cellular interactions found during in vivo development while providing purity of the desired product construct so as to enable utilization of the product, for instance as transplantable tissue. For example, it is commonly desired that the product cells be isolated and free from extraneous cells of other phenotypes, and in particular those previously shown to exhibit unfavorable attributes following implant (e.g., tumor generation or immune system reaction). However, biochemical interaction between those less than desirable cell types with the product cells may be necessary for the healthy growth and development of the product cells, for example due to their introduction of growth stimulation factors into the culture environment.

Many existing co-culture systems are simple well plate designs that are static in nature and do not allow for manipulation of the local environment beyond the gross chemical inputs to the system. As such, the development of more dynamic co-culture systems has become of interest. However, known dynamic systems, similar to the static systems, often provide only a single source of nutrients/growth stimulants/etc. to all of the cell types held in the system. Moreover, the different cell types that are co-cultured in both static and dynamic systems are usually maintained in actual physical contact with one another, preventing the development of an isolated cell population, and also limiting means for better understanding the biochemical communications between the cell types during growth and development.

There are some systems in which an attempt has been made to physically separate cell types in dynamic systems, for instance through location of a porous substrate between the two cell types. However, in these systems, all cell-types cultured in the system are still subjected to the same culture media, similar to the above-described static systems. Additionally, the porous substrate usually also serves as the support scaffold to which cells are intended to attach and grow. Attachment of cells to the porous substrate will alter the flow characteristics of biochemicals across and through the substrate, which in turn affects communication between the cells.

What is needed in the art is a method for co-culturing multiple cell types in a dynamic environment in which the different cell types can communicate biochemically, and yet can be separated physically. Moreover, what is needed is a system in which cells can be developed to form a three-dimensional construct, while maintaining the isolation and purity of the developing product cells and at the same time allowing for biochemical communication between cells of different types.

SUMMARY

In one aspect, the present invention is directed to co-culture bioreactor systems that can maintain different cell types in physically isolated environments but can allow biochemical communication between the different cell types. For instance, a co-culture bioreactor system of the invention can include a first culture chamber that defines a first inlet and a first outlet such that fluid can flow through the culture chamber. The system can also include a second culture chamber defining a second inlet and a second outlet allowing a second fluid flow through this second chamber. The system can also include a semi-permeable membrane. The semi-permeable membrane can be located between the first culture chamber and the second culture chamber. The semi-permeable membrane can have a porosity so as to allow passage of cellular expression products through the membrane, but so as to prevent passage of the cells held in either chamber through the membrane. In one embodiment, the semi-permeable membrane can be formed of a material, for example a polycarbonate, which can discourage cellular attachment to the membrane.

The bioreactor systems of the invention can include a cellular anchorage in one or both of the culture chambers. Suitable cellular anchorage can be formed of multiple discrete scaffolds or single continuous scaffolds. Multiple discrete scaffolds can be maintained within a culture chamber through utilization of a retaining mesh that can hold the scaffolding materials within the chamber and prevent the loss of the scaffolding materials through the outlet.

In one embodiment, a cellular anchorage can be maintained at a distance from the semi-permeable membrane that separates the chambers. This distance can then prevent attachment of cells to the membrane and maintain the physical isolation of different cell types within their respective culture chambers.

The systems can also be capable of incorporating additional culture chambers that can be in biochemical communication with one or both of the other two culture chambers. For instance, a third chamber can house cells that can be in biochemical communication with the first culture chamber, optionally with a semi-permeable membrane separating the first and third chambers, though this aspect is not a requirement of the system.

The bioreactors of the invention can also include the capability of subjecting the cells within the culture chambers to multiple mechanical stimuli. For instance, fluid perfusion through a culture chamber can subject developing cells to shear stress, an adjacent pressure module can be utilized to subject the interior of a culture chamber to hydrostatic loading, and the like.

The bioreactors can be used for growth and development of isolated cells in various different applications. For instance, three-dimensional cellular constructs can be formed including only the cells that are isolated in one of the culture chambers of the reactor system. In one embodiment, a culture chamber can be seeded with undifferentiated cells, and the method can include triggering differentiation of the cells via the biochemical triggers provided from the cells of the second culture chamber.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying figures, in which.

Figure 1:
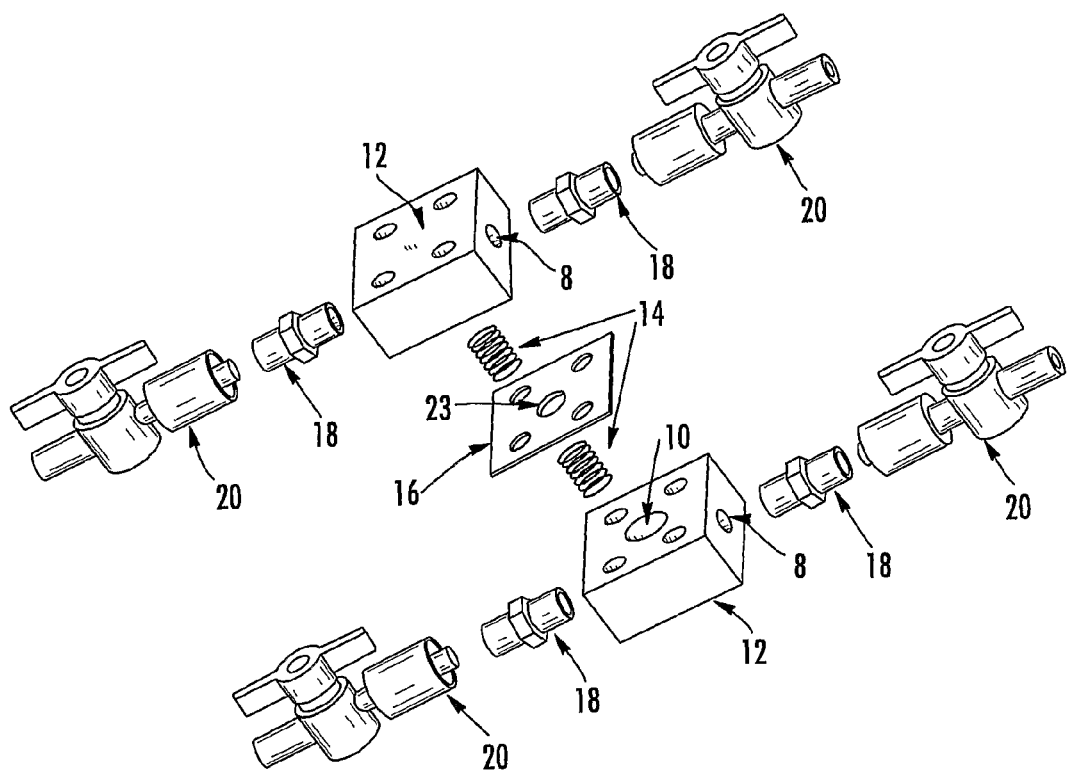
FIG. 1 is an exploded view of one embodiment of the present invention including two cell modules.

Repeat use of reference characters in the present specification and drawings is intended to represent the same or analogous features or elements of the present invention.

DETAILED DESCRIPTION OF THE INVENTION

Reference will now be made in detail to various embodiments of the invention, one or more examples of which are set forth below. Each embodiment is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used in another embodiment to yield a still further embodiment.

In one aspect, the present invention is directed to multi-chambered co-culture systems. The systems of the invention can be utilized for the growth and development of isolated cells of one or more cell types in a dynamic in vitro environment more closely resembling that found in vivo. For instance, the multi-chambered systems of the present invention can allow biochemical communication between cells of different types while maintaining the different cell types in a physically separated state, and moreover, can do so while allowing the cell types held in any one chamber to grow and develop with a three-dimensional aspect. In addition, the presently disclosed devices and systems can allow for variation and independent control of environmental factors within the individual chambers. For instance, the chemical make-up of a nutrient medium that can flow through a chamber as well as the mechanical force environment within the chamber including the perfusion flow, hydrostatic pressure, and the like, can be independently controlled and maintained for each separate culture chamber of the disclosed systems.

In one application the co-culture systems of the invention can be utilized for culturing product cells for medical use, for instance, for transplant to a patient or for manufacture of a protein product, such as a biopharmaceutical. According to this embodiment, cells can be grown in an environment that includes the biochemical products of different cell types, at least some of which may be necessary for the growth and development of the desired cells. However, cell types can be maintained in a physically isolated state during their growth and development. As such, possible negative consequences due to the presence of aberrant or undesired cell types in the desired product cells can be avoided.

In another application, the disclosed invention can be used to more closely study the biochemical communication between different cell types and the influence of this biochemical communication on the growth and development of cells. As the local environment within each culture chamber of the system can be independently controlled while biochemical communication between chambers can be maintained, information regarding the growth and development of cells and the influence of the local environment on that growth and development can be examined through use of the devices and systems of the invention.

In yet another embodiment, undifferentiated stem cells can be located in a first chamber, and one or more types of feeder cells can be located in adjacent chamber(s). Such a system can be utilized to, for example, study the triggering mechanisms involved in stem cell differentiation or to provide isolated, differentiated cells for implantation.

Referring to FIG. 1, an exploded view of one embodiment of the present invention is illustrated. This particular embodiment of a co-culture system includes two individual culture chambers 10 (only one of which is visible in this particular view), each of which is defined by a cell module 12. The dimensions and overall size of a cell module 12, and culture chamber 10, are not critical to the invention. In general, a cell module 12 can be of a size so as to be handled and manipulated as desired, and so as to provide access to the culture chambers either through disassembly of the device, through a suitably located access port, or according to any other suitable method. In addition, a culture chamber 10 defined by the module 12 can generally be of any size as long as adequate nutrient flow can be maintained throughout a three-dimensional cellular construct growing in the culture chamber 10, so as to prevent cell death at the construct center due to lack of nutrient supply.

Though each cell module 12 of the embodiment illustrated in FIG. 1 includes only a single culture chamber 10, in other embodiments, a single cell module 12 can include multiple culture chambers. According to such an embodiment each culture chamber of the module can include individual access ports (described further below), so as to provide individualized flow through each culture chamber and independent control of the local environmental conditions in each culture chamber.

While the materials from which the module 12 can be formed can generally be any moldable or otherwise formable material, the surface of the culture chamber 10, as well as any other surfaces of the module that may come into contact with the cells, nutrients, growth factors, or any other fluids or biochemicals that may contact the cells, should be of a suitable sterilizable, biocompatible material. In one particular embodiment, components of the system can also be formed so as to discourage cell anchorage at the surfaces.

The culture chamber 10 can generally be of a shape and size so as to cultivate living cells within the chamber. In one preferred embodiment, culture chamber 10 can be designed to accommodate a biomaterial scaffold within the culture chamber 10, while ensuring adequate nutrient flow throughout a cellular construct held in the culture chamber 10. For instance, a culture chamber 10 can be between about 3 mm and about 10 mm in cross section. In another embodiment, the culture chamber can be greater than about 5 mm in any cross sectional direction. For instance, the chamber can be cylindrical in shape and about 6.5 mm in both cross sectional diameter and height. The shape of culture chamber 10 is not critical to the invention, as long as flow can be maintained throughout a cellular construct held in the chamber.

The system can also include a cell anchorage that can be contained in the culture chamber 10. The term "cell anchorage" as utilized herein refers to one or more articles upon which cells can attach and develop. For instance, the term "cell anchorage" can refer to a single continuous scaffold, multiple discrete scaffolds, or a combination thereof. The terms "cell anchorage," "cellular anchorage," and "anchorage" are intended to be synonymous. Any suitable cell anchorage as is generally known in the art can be located in the culture chamber 10 to provide anchorage sites for cells and to encourage the development of a three-dimensional cellular construct within the culture chamber 10.

For purposes of the present disclosure, the term continuous scaffold is herein defined to refer to a construct suitable for use as a cellular anchorage that can be utilized alone as a single, three-dimensional entity. A continuous scaffold is usually porous in nature and has a semi-fixed shape. Continuous scaffolds are well known in the art and can be formed of many materials, e.g., coral, collagen, calcium phosphates, synthetic polymers, and the like, and are usually pre-formed to a specific shape designed for the location in which they will be placed. Continuous scaffolds are usually seeded with the desired cells through absorption and cellular migration, often coupled with application of pressure through simple stirring, pulsatile perfusion methods or application of centrifugal force.

Discrete scaffolds are smaller entities, such as beads, rods, tubes, fragments, or the like. When utilized as a cellular anchorage, a plurality of identical or a mixture of different discrete scaffolds can be loaded with cells and/or other agents and located within a void where the plurality of entities can function as a single cellular anchorage device. Exemplary discrete scaffolds suitable for use in the present invention that have been found particularly suitable for use in vivo are described further in U.S. Pat. No. 6,991,652 to Burg, which is incorporated herein by reference. A cellular anchorage formed of a plurality of discrete scaffolds can be preferred in certain embodiments of the present invention as discrete scaffolds can facilitate uniform cell distribution throughout the anchorage and can also allow good flow characteristics throughout the anchorage as well as encouraging the development of a three-dimensional cellular construct.

In one embodiment, for instance when considering a cellular anchorage including multiple discrete scaffolds, the anchorage can be seeded with cells following assembly and sterilization of the system. For example, an anchorage including multiple discrete scaffolds can be seeded in one operation or several sequential operations. Optionally, the anchorage can be pre-seeded, prior to assembly of the system. In one embodiment, the anchorage can include a combination of both pre-seeded discrete scaffolds and discrete scaffolds that have not been seeded with cells prior to assembly of the system.

The good flow characteristics possible throughout a plurality of discrete scaffolds can also provide for good transport of nutrients to and waste from the developing cells, and thus can encourage not only healthy growth and development of the individual cells throughout the anchorage, but can also encourage development of a unified three-dimensional cellular construct within the culture chamber.

The materials that are used in forming an anchorage can generally be any suitable biocompatible material. In one embodiment, the materials forming a cellular anchorage can be biodegradable. For instance, a cellular anchorage can include biodegradable synthetic polymeric scaffold materials such as, for example, polylactide, chondroitin sulfate (a proteoglycan component), polyesters, polyethylene glycols, polycarbonates, polyvinyl alcohols, polyacrylamides, polyamides, polyacrylates, polyesters, polyetheresters, polymethacrylates, polyurethanes, polycaprolactone, polyphophazenes, polyorthoesters, polyglycolide, copolymers of lysine and lactic acid, copolymers of lysine-RGD and lactic acid, and the like, and copolymers of the same. Optionally, an anchorage can include naturally derived biodegradable materials including, but not limited to chitosan, agarose, alginate, collagen, hyaluronic acid, and carrageenan (a carboxylated seaweed polysaccharide), demineralized bone matrix, and the like, and copolymers of the same.

A biodegradable anchorage can include factors that can be released as the scaffold(s) degrade. For example, an anchorage can include within or on a scaffold one or more factors that can trigger cellular events. According to this embodiment, as the scaffold(s) forming the cellular anchorage degrades, the factors can be released to interact with the cells.

Referring again to FIG. 1, in those embodiments including a cellular anchorage formed with a plurality of discrete scaffolds, a retaining mesh 14 can also be located within the culture chamber 10. The retaining mesh 14 can be formed of any suitable biocompatible material, such as polypropylene, for example, and can line at least a portion of a culture chamber 10, so as to prevent material loss during media perfusion of the culture chamber 10. A porous retaining mesh 14 can generally have a porosity of a size so as to prevent the loss of individual discrete scaffolds within the culture chamber 10. For example, a retaining mesh 14 can have an average pore size of between about 100 μm and about 150 μm.

Upon assembly of the system, two (or more) culture chambers 10 can be aligned so as to be immediately adjacent to one another. Between two adjacent culture chambers can be a gasket 16 including a permeable membrane portion 23. The membrane portion 23 of gasket 16 can be aligned between the culture chambers 10 and can have a porosity that can allow biochemical materials, for instance growth factors produced by a cell in one chamber, to pass through the membrane and into the adjacent chamber, where interaction can occur between the material produced in the first chamber and the cells contained in the second chamber. The membrane porosity can be small enough to prevent passage of the cells or cell extensions from one chamber to another. In particular, the membrane porosity can be predetermined so as to discourage physical contact between the cells held in adjacent chambers, and thus maintain isolation of the cell types. Suitable porosity for a membrane can be determined based upon specific characteristics of the system, for instance the nature of the cells to be cultured within the chamber(s). Such determination is well within the ability of one of ordinary skill in the art and thus is not discussed at length herein.

Physical isolation of cellular contents of adjacent chambers can also be encouraged through selection of membrane materials. For instance, materials used to form the membrane 23 can be those that discourage anchorage of cells onto the membrane 23. Attachment of cells to the membrane 23 can be discouraged to prevent physical contact between cells held in adjacent culture chambers as well as to prevent interference with flow between the adjacent chambers. Flow interference could interfere with the biochemical communication between the adjacent culture chambers. One exemplary material that can discourage cellular attachment is a polycarbonate membrane. Other suitable materials are generally known to those of skill in the art.

In another embodiment the cells contained in a culture chamber 10 can be maintained at a distance from the membrane 23 to discourage physical contact between cells held in adjacent culture chambers. For instance retaining mesh 14 can be located between a cell anchorage held in a culture chamber and the membrane located between two adjacent chambers. The width of the retaining mesh 14 can prevent contact of the cells with the membrane 23. Optionally, the retaining mesh 14 can be at a distance from the membrane 23, providing additional separation between the membrane 23 and cells held in the culture chamber 10. In another embodiment, a continuous scaffold can be located in a culture chamber 10 at a distance from the membrane 23 so as to discourage physical contact between the cells held in the culture chamber and the membrane 23. While a preferred distance between the membrane 23 and cells held in the chamber will vary depending upon the specific characteristics of the system as well as the cells to be cultured in the system, in general, the distance between the two can be at least about 100 microns.

Each culture chamber 10 of the system can include the capability for independent flow control through the chamber. For example, and referring again to FIG. 1, each individual culture chamber 10 can include an inlet 8 and an outlet (not shown) through which medium can flow. In this particular embodiment, the inlet 8 and outlet are connected to medium perfusion tubing via quick-disconnect luers 18 and stopcock valves 20, but this particular arrangement is not a requirement of the invention, and any suitable connection and perfusion system as is generally known in the art can be utilized. For example, in another embodiment, the connection can be an integral portion of a single formed module 12.

Figure 2:
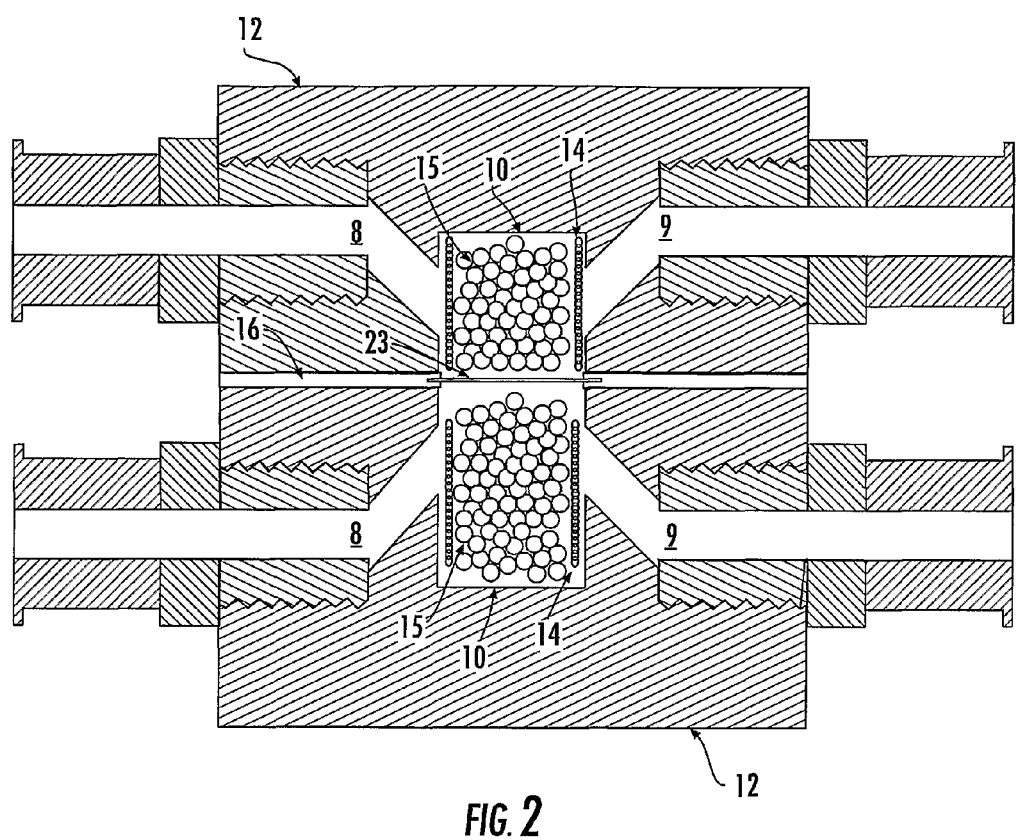
FIG. 2 is a schematic diagram of the embodiment of FIG. 1 following assembly such that the two cell modules are adjacent and allow biochemical communication between cells held in the two adjacent modules.

Referring to FIG. 2, the embodiment illustrated in FIG. 1 in exploded view is shown following assembly. As can be seen, the embodiment includes two modules 12, each of which includes a single culture chamber 10. Upon assembly, the two culture chambers 10 are aligned with the permeable membrane portion 23 of gasket 16 therebetween. In this particular embodiment, a plurality of discrete scaffolds 15 has been located within each of the two culture chambers 10 as a cellular anchorage. In addition, each culture chamber 10 can be lined with a retaining mesh 14, as shown. Upon assembly, desired media can be independently perfused through each culture chamber 10 via the separate inlets 8 and outlets 9.

Figure 3:
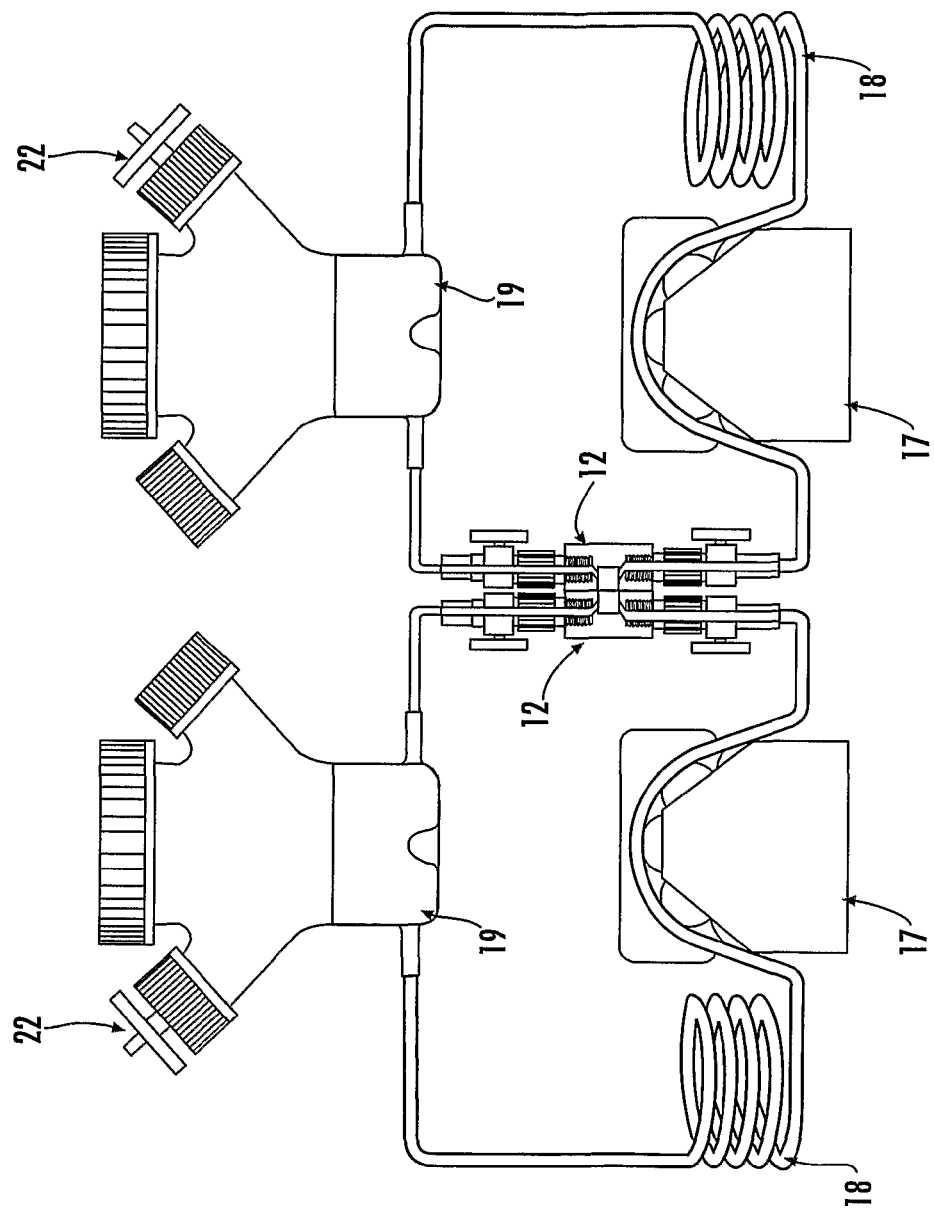
FIG. 3 is one embodiment of a system of the present invention including two adjacent cell modules having independently controlled flow characteristics therethrough.

FIG. 3 illustrates one embodiment of a co-culture system according to the present invention. This particular embodiment includes two assembled modules 12, such as those illustrated in FIG. 2, each in line in a flow circuit that is completely independent of the other including a pump 17, for instance a peristaltic pump, and a media container 19. In this particular embodiment, gas exchange can be facilitated by two methods, including a first method utilizing a coiled length of a gas permeable tubing 18 such as, for example, a platinum-cured silicone tubing, as well as a second method including an air filter 22 located, in this embodiment, at the media container 19. Any gas exchange method as is known can alternatively be utilized, however.

One of the many benefits of the disclosed invention is the versatility of the system. For example, in the embodiment illustrated in FIG. 3, the design attributes can allow convenient and flexible reversal of the perfusion flow for a particular experimental protocol. In addition, the disclosed systems can be utilized to allow biochemical communication with physical separation between two or more different cell types for a variety of applications including, for example, bone development (osteocyte/preosteoblast or stem cell/preosteoclast), breast tissue replacement (preadipocyte/endothelial), stem cell research (embryonic stem cells/feeder cells), and regeneration or replacement of damaged liver cells (hepatocyte/endothelial).

Figure 4:
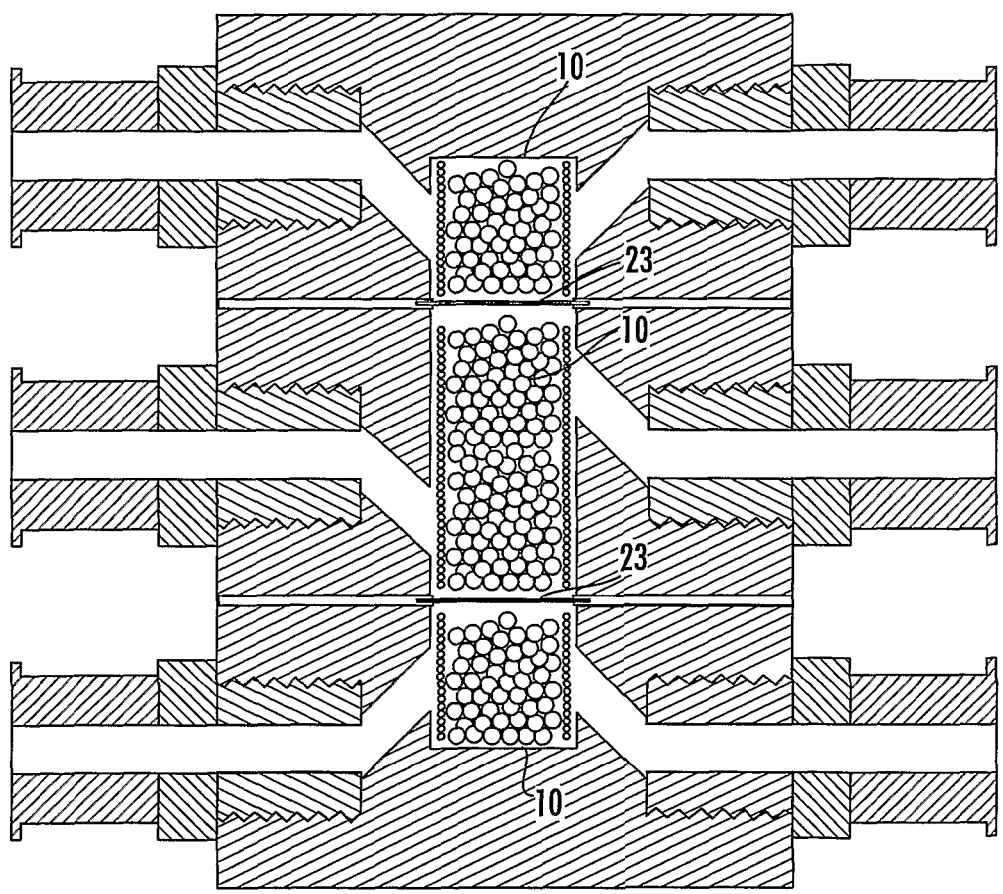
FIG. 4 is a schematic of a system as herein disclosed including multiple cell culture chambers in biochemical communication with one another.

The culture systems of the present invention are not limited to co-culture systems in which only two independently controlled culture chambers are located adjacent to one another. In other embodiments of the invention, additional cell modules can be added to the system such that a single culture chamber can be in biochemical communication with the contents of two or more other culture chambers, for instance in a stacked arrangement as is illustrated in FIG. 4.

Figures 5A, 5B:
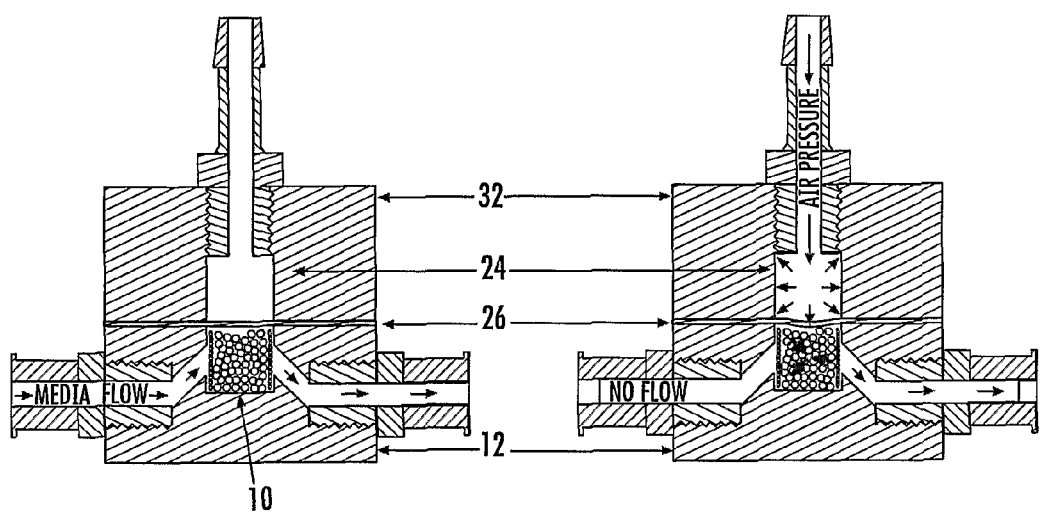
FIG. 5 illustrates another embodiment of the present invention in which at least one of the cell modules of the system can be subjected to periodic variation in hydrostatic pressure.

In another embodiment, one or more of the culture chambers of the system can be designed so as to provide the capability of subjecting the interior of the culture chamber to variable dynamic mechanical stimuli such as mechanical loading or variation in fluid flow through the culture chamber in order to vary the associated stress on the developing cells. Such an embodiment can be utilized to, for instance, trigger differentiation and development of stem cells contained in a culture chamber. For example, according to one embodiment, illustrated in FIG. 5, a cell module 12 can be located immediately adjacent to a second cell module (not shown in FIG. 5), as described above. In addition, the cell module 12 can, on a second side of the module 12, be aligned with a pressure module 32 that can be utilized to vary the hydrostatic pressure on the contents of the culture chamber 10. According to this embodiment, the culture chamber 10 can be aligned with a pressure chamber 24 defined by pressure module 32, and the two adjacent chambers 10, 24 can be separated by an impermeable diaphragm 26. The introduction of pressurized fluid, e.g., air, into the pressure chamber 24, can deflect the diaphragm 26, as shown in FIG. 5B, and transfer the pressure to the volume of fluid in the culture chamber 10. In one embodiment, fluid flow through the culture chamber 10, as well as through other adjacent culture chambers, can be stopped prior to pressurizing the system, so as to develop a fixed volume of fluid within the affected portion of the system. In addition, cyclical hydrostatic loading patterns can be established, if desired, by simply cycling the pressurized fluid through the pressure chamber 24 through use of a solenoid valve and a time-delay relay, computer automation, or any other method that is generally known to one of ordinary skill in the art.

Such an embodiment may be particular beneficial in orthopedic related research studies. This system can provide improved ex vivo simulation of the physiological in vivo environment for bone that includes both hydrostatic compression and perfusion fluid flow as a result of normal skeletal loading. For example, in one embodiment of the system, a hydrostatic loading cycle of 0.5 Hz and fluid pressures exceeding 300 kPa can be demonstrated. These values closely approximate those found in the lacunar-canalicular porosity of the human femur during normal gait, i.e., 0.5-2.0 Hz and 270 kPa.

In one embodiment of the present invention, multiple independent co-culture systems can be provided that can incorporate various combinations of experimental stimuli, so as to provide real time comparisons of the differing stimuli on the developing cellular constructs.

In another embodiment, a bank of multiple and identical systems can be established, so as to provide adequate replication of a single experimental procedure and/or to provide larger cumulative amounts of the product cells that are grown, developed or otherwise produced within each of the individual culture chambers.

Example 1

Cell Culture: A 3T3 mouse fibroblast cell line (available from ATCC, Manassas, Va.) was used in three studies (numbered 1-3 below) to examine cell viability when subjected to perfusion fluid flow in a system. A fourth study (Study 4) used a D1 cell line (ATCC) of adult mouse bone marrow stromal cells and incorporated hydrostatic compression in addition to the perfusion flow. The D1 cell line was selected due to its demonstrated multi-potent potential including favorable osteogenic properties.

within a culture chamber. Four sets of clamping socket screws, washers and nuts were used to form a tightly sealed assembly. The assembled bioreactor, including adjacent luers, stopcock valves and enclosed PLL beads, was sterilized with ethylene oxide gas at room temperature and degassed for several days under 25 inches Hg vacuum. Flow circuit tubing and quick-disconnect luers were also sterilized with ethylene oxide gas while the medium storage bottle was autoclaved.

The complete bioreactor flow circuit including a single cell module located immediately adjacent to a single pressure module such as that illustrated in FIG. 5 but with only a single culture chamber, was assembled in a standard laminar flow hood to prevent contamination. A volume of 60 ml of medium was added to the storage bottle. Initial culture medium for studies 1-3 consisted of Dulbecco's Modified Eagle's Medium (DMEM) (Invitrogen, Carlsbad, Calif.) supplemented with 10% fetal bovine serum (FBS) (Mediatech, Herndon, Va.), 5 ml antibiotic/antimycotic (Invitrogen), 1 ml fungizone (Invitrogen), 5 ml L-glutamine (Invitrogen) and 10 µg fibroblast growth factor (Fisher). Initial culture medium used for study 4 was Dulbecco's Modified Eagle's Medium (ATCC) supplemented with 10% FBS. For all studies, the system was primed with medium to prewet the PLL beads prior to cell seeding. Cell seeding was accomplished by pipetting the appropriate cell suspension into the medium storage bottle and then allowing the system to perfuse the cells through the flow circuit to the discrete scaffolds within the cell module. The entire perfusion flow circuit was contained in an incubator that was maintained at 37° C. and 5% $CO_2$. Each of the four preliminary studies differed either in cell type, quantity, passage, duration or mechanical stimulus as described below in Table 1.

TABLE 1

| Study | Cell Type | Passage | Cell Seeding Density (per ml scaffold volume) | Cell Quantity Seeded | Duration | Mechanical Stimulus |
|---|---|---|---|---|---|---|
| 1 | 3T3 | 37 | 1.2E7 | 2.4E6 | 7 days | Perfusion |
| 2 | 3T3 | 29 | 3.0E6 | 6.0E5 | 21 days | Perfusion |
| 3 | 3T3 | 31 | 3.0E6 | 6.0E5 | 21 days | Perfusion |
| 4 | D1 | 24 | 3.0E6 | 6.0E5 | 28 days | Perfusion & Hydrostatic |

Anchorage Fabrication Multiple discrete poly-L-lactide (PLL) hollow beads with an average diameter of 0.8 mm served as the discrete tissue engineering scaffolds for all studies. Briefly, scaffold fabrication was completed using solvent emulsion techniques, beginning with an 8% (m/v) solution of Purasorb polylactide pellets (Cargill, Minneapolis, Minn.) and dichloromethane (Mallinckrodt Baker, Phillipsburg, N.J.). A quantity of 5 ml of PLL solution was dispensed, using a 20 cc glass syringe (BD, Franklin Lakes, N.J.) and 16-gauge needle (BD), into 500 ml of a stirred 0.1% aqueous solution of polyvinyl alcohol (PVA) (Sigma-Aldrich, St. Louis, Mo.). PVA solution in the amount of 300 ml was siphoned out of the beaker, after which, 200 ml of 2% isopropyl alcohol solution (VWR, West Chester, Pa.) was added. Following three minutes of stirring, 300 ml of solution was siphoned out and 400 ml of PVA solution was added back to the remaining 100 ml volume. The total volume of 500 ml was then stirred for three minutes, resulting in PLL bead formation. The hollow beads were strained from the solution and allowed to dry under vacuum to remove any residual solvent.

Modular bioreactor assembly was completed with the inclusion of a porous volume of 0.2 ml of PLL hollow beads Study 1 provided initial observations regarding metabolism and viability of cells cultured within the confines of the culture chamber. A medium perfusion volumetric flow rate of 4.8 ml per minute was continuous throughout the seven-day duration. The medium was not changed for the seven-day duration of the study. Lactic acid and glucose levels were measured at days 0 and 7 using a YSI 2700 SELECT Biochemistry Analyzer (YSI, Yellow Springs, Ohio). Visual inspection of live fibroblast attachment to the PLL beads was demonstrated at day 7 through the use of a LIVE/DEAD® Viability/Cytotoxicity Kit (Invitrogen) and fluorescent microscopy. A seven-day acellular control study was conducted in parallel to confirm that rising lactic acid levels were due to cell metabolic activity and not PLL hydrolysis.

Studies 2 and 3 extended the culture time to 21 days and provided opportunity to refine endpoint assay techniques. As in Study 1, the volumetric flow rate of 4.8 ml per minute was continuous for the 21-day duration with the exception of brief periods during medium changes and aliquot retrieval. Medium aliquots were taken every two days, beginning on day 4, and complete medium changes occurred on days 8 and 16. Aliquots were monitored for metabolic solute levels, and live/dead fluorescent microscopy was completed on day 21.

Unlike previous studies, study 4 incorporated hydrostatic compression in the experimental protocol beginning on day 4. Daily routine involved 8 hours of cyclic hydrostatic compression, approximately 330 kPa at 0.1 Hz (5 seconds on, 5 seconds off), followed by 16 hours of continuous perfusion flow at 4.8 ml per minute. Hydrostatic compression was interrupted after 4 hours with 5 minutes of perfusion flow to deliver fresh nutrients to the cells and prevent the buildup of waste products. A control system was used that did not receive hydrostatic compression loading. The control system's stopcock valves adjacent to the cell module were closed during the eight-hour hydrostatic segment but no pressure was applied. The inclusion of D1 adult mouse bone marrow stromal cells was strategic due to the demonstrated osteogenic characteristics. These properties provided opportunities to observe changes in phenotype differentiation in response to the applied mechanical loading regimens. Beginning at day 3, osteogenic media for both the experimental and control systems were supplemented with 50 µg/ml L-ascorbic acid (Sigma) and 10 mM β-glycerophosphate (Sigma). Assays commonly used to evaluate osteogenic differentiation, including alkaline phosphatase activity, calcium content and total protein, were practiced for application in future experiments. Metabolic activity was observed through assessment of medium aliquots as well as relative AlamarBlue™ (Biosource, Camarillo, Calif.) fluorescent emission.

The graphs of FIGS. 6-10 represent mean±standard error of the mean with n=1, where n represents the number of replications of a given study. Nested measurements were made within each study at the respective time points; thus, variability is due to subsampling within the experimental assay. Therefore, no statistical comparisons could be made for the preliminary experiments. Microsoft Excel was used for all numerical analysis.

Figure 6:
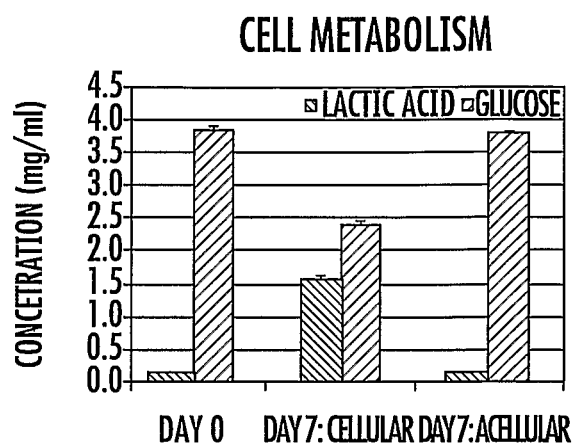
FIG. 6 illustrates cellular metabolic activity over a seven-day duration for bioreactor cell study 1 as described in Example 1.
Figure 7:
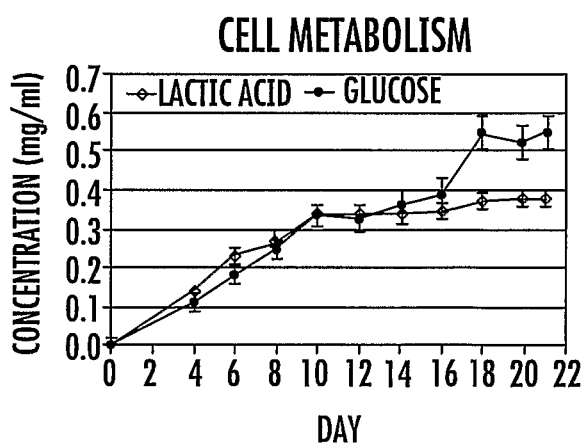
FIG. 7 illustrates average cumulative metabolic data over 21-day duration for bioreactor cell studies 2 and 3 as described in Example 1.
Figure 8:
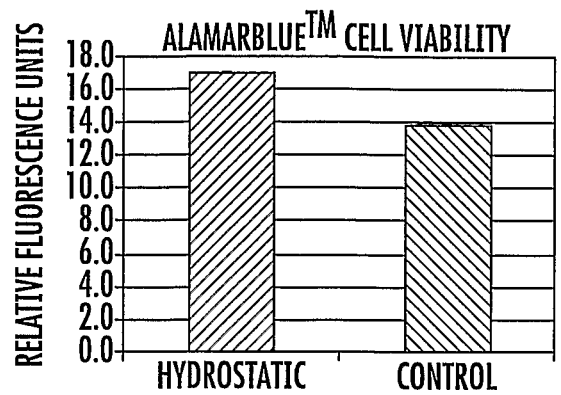
FIG. 8 illustrates cell viability on day 28 for the experimental and control setups for bioreactor cell study 4 as described in Example 1.
Figure 9:
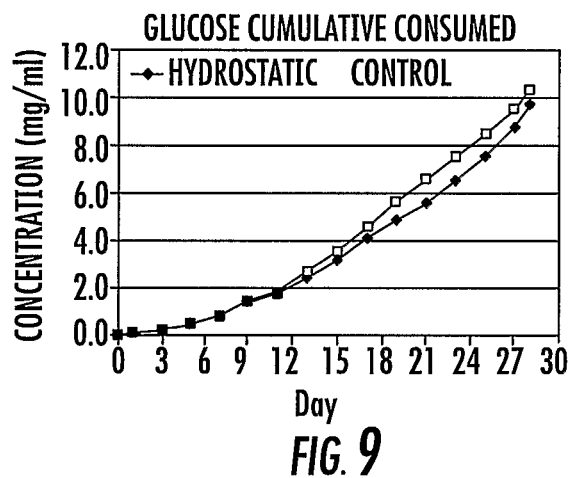
FIG. 9 illustrates cumulative glucose consumed over 28-day duration for bioreactor cell study 4 as described in Example 1.
Figure 10:
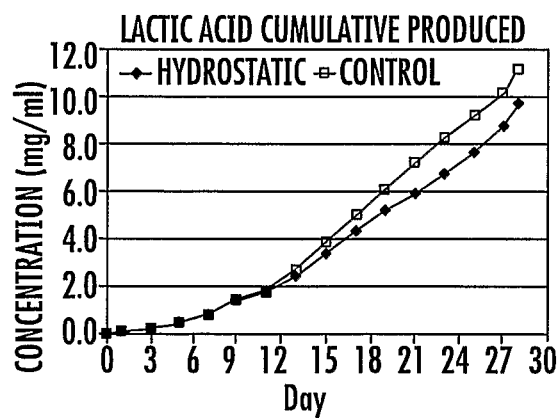
FIG. 10 illustrates cumulative lactic acid produced over 28-day duration for bioreactor cell study 4 as described in Example 1.
Figure 11:
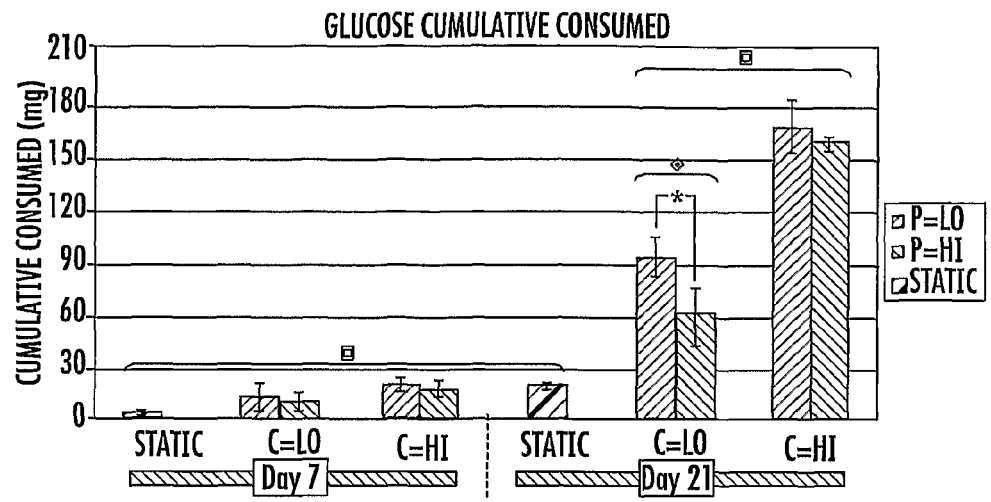
FIG. 11 illustrates cumulative glucose consumed in the bioreactor study described in Example 2.
Figure 12:
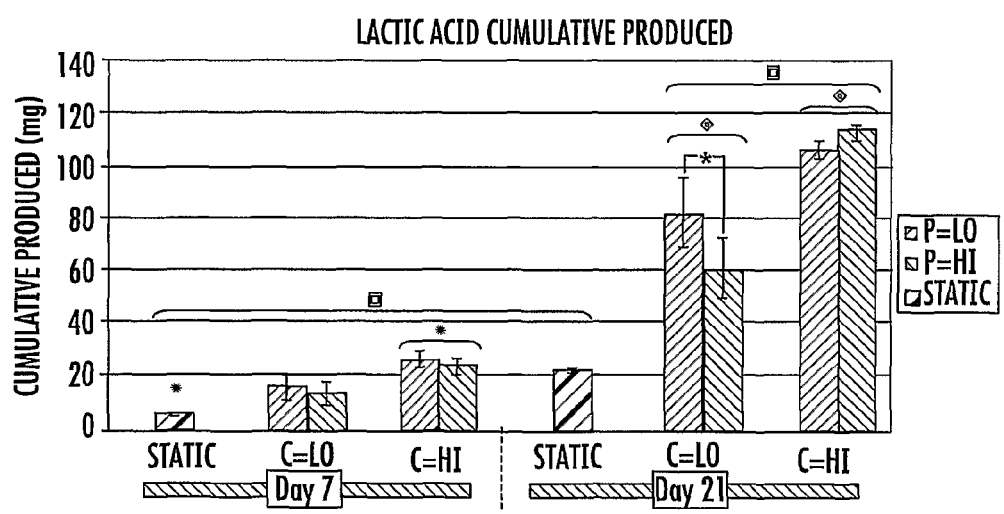
FIG. 12 illustrates cumulative lactic acid produced in the bioreactor study described in Example 2.
Figure 13:
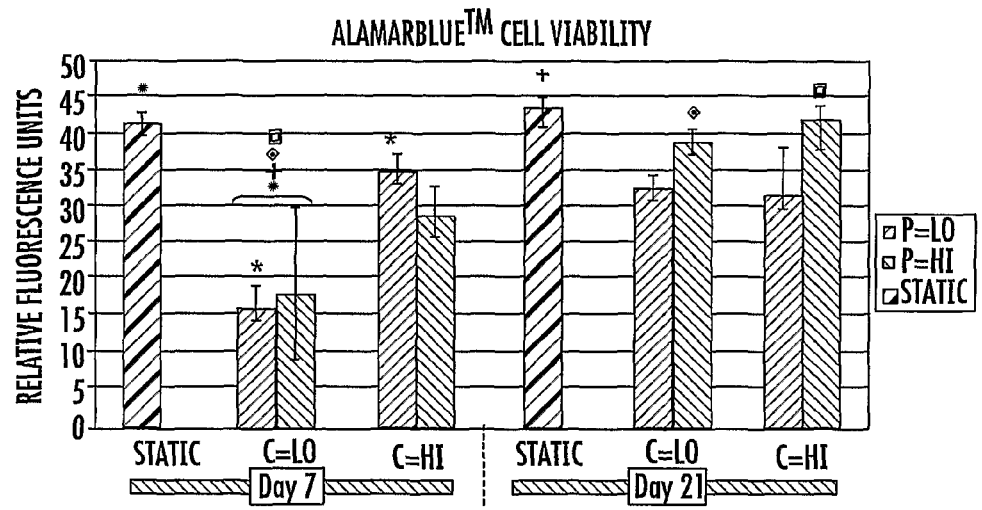
FIG. 13 illustrates AlamarBlue™ cell viability assay results in the bioreactor study described in Example 2.

The acellular control setup for study 1 presented no numerical elevation in lactic acid levels due to PLL hydrolysis (FIG. 6). Cumulative levels of glucose consumption and lactic acid production increased over the 21-day duration of studies 2 and 3 (FIG. 7). Live/dead imaging depicted a confluent cell layer at the PLL bead surface (not shown). Comparative cellular metabolic activity of the experimental and control systems of study 4 demonstrated similar numerical values for cumulative metabolic solutes and alamarBlue™ relative fluorescence units (FIGS. 8-10).

As can be seen, the modular bioreactor provided an in vitro environment conducive for cell growth on three-dimensional scaffolds. Metabolic data demonstrated that cells continued to flourish over the duration of each preliminary study. Endpoint evaluations with AlamarBlue™ and live/dead fluorescent microscopy provided additional evidence as to the ongoing viability of cells cultured in the bioreactor system.

Example 2

Dynamic bioreactor systems were utilized to examine the influence of multiple mechanical stimuli on the differentiation traits of adult mesenchymal stem cells in addition to a variety of other cell types. The bioreactor was designed to model the in vivo conditions through available system conditions including hydrostatic loading. Perfusion of medium through the system was also adjusted to provide physiological levels of fluid shear stress across the cells.

Bioreactor systems such as that illustrated in FIG. 5 were prepared. Each 0.2 mL volume culture chamber was loaded with 45 mg PolyGraft™ granular material. A silicone diaphragm/gasket and four clamping socket screws were used to provide leak-free assembly of the culture chamber adjacent a pressure module.

All systems utilized a D1 cell line grown in quantity using standard cell culture flasks (Corning). The initial cell culture medium consisted of DMEM (ATCC) supplemented with 10% FBS and 1% antibiotic/antimycotic. Each bioreactor flow circuit, including the culture chamber loaded with the granular scaffold, was primed and pre-wetted with medium prior to cell seeding. Each medium storage bottle was filled with 30 mM of the initial cell culture medium. Each bioreactor setup was seeded with a total of 6.0E5 cells by injecting one milliliter of the cell suspension directly into the flow circuit and culture chamber.

Five different treatment regimens were designed having different combinations of perfusion flow rate and hydrostatic compression characteristics. According to the regimens, perfusion flow was set to static, low or high. Low perfusion flow was set as 0.35 mL/min, and high perfusion flow was 0.70 mL/min. For those treatment regimens requiring only perfusion flow (i.e., no hydrostatic compression component), continuous perfusion of the bioreactor flow circuit occurred for the duration of the study with the exception of medium changes and aliquot sampling.

Hydrostatic compression was either low, at 0 kPa, or high, at 200 kPa. Treatment regimens applying both perfusion flow and hydrostatic compression underwent a daily schedule including 22 hours of continuous perfusion flow followed by two hours of cyclic hydrostatic compression. Within the two hour time period, cyclic hydrostatic compression was applied for 10 minute increments followed by a five minute session of perfusion flow to provide cells with fresh nutrients and remove damaging waste products. The experimental protocol of shifting from compression to perfusion and back to compression was repeated for the duration of the two hour period. Compression was applied at 200 kPa and cycled at 0.5 Hz (one second on and one second off). Specific treatment regimens were as shown below in Table 1.

TABLE 1

| Regimen Number | Perfusion (mL/min) | Compression (kPa) |
|---|---|---|
| 1 | 0.35 | 0 |
| 2 | 0.70 | 0 |
| 3 | 0.35 | 200 |
| 4 | 0.70 | 200 |
| 5 | Static | Static |

The initial supplemented medium of DMEM, FBS and antibiotic/antimycotic was used through day 2. At day 2, the initial medium was modified with the following additional supplements to formulate an osteogenic differentiation medium: 50 µg/ml L-ascorbic acid 2-phosphate, 3 mM β-glycerophosphate, 10 nM Dexamethosone. Complete change of the supplemented medium took place on days 2, 8, 14 and 20.

Lactic acid production and glucose consumption were monitored throughout the course of the runs by taking medium samples every two or three days. Each treatment regimen was carried out in six bioreactor setups. Each regimen was assayed at day 7 and day 21 to provide a variety of quantitative, comparable data across all treatment combinations. Upon reaching a designated endpoint of either day 7 or 21, each of three of the setups were disassembled, and a variety of assay methodologies were carried out.

FIGS. 11-17 graphically illustrate the assay results obtained for determination of cumulative glucose consumed, cumulative lactic acid produced, AlamarBlue™ cell viability, total protein content, alkaline phosphatase activity, calcium content, and phosphorous content, respectively.

Visual observation of the cell-scaffold constructs upon removal from the culture chamber recognized that the constructs retained much of the bulk shape as packed in the culture chamber. Samples undergoing high hydrostatic compression appeared to maintain a tighter packing of the granular cluster following transfer from the culture chamber.

The inclusion of mechanical stimuli in the experimental protocol clearly upregulated the cumulative metabolic requirements of cells when compared to static culture conditions. Hydrostatic compression also appeared to further increase the rate of glucose consumption and lactic acid production as can be seen with reference to FIGS. 11 and 12. While the dynamic experimental conditions appeared to possess higher metabolic rates, the endpoint cell viability ascertained through the AlamarBlue™ assay conveyed a result of consistency regardless of whether dynamic or static conditions were applied, as can be seen with reference to FIG. 13.

Figure 14:
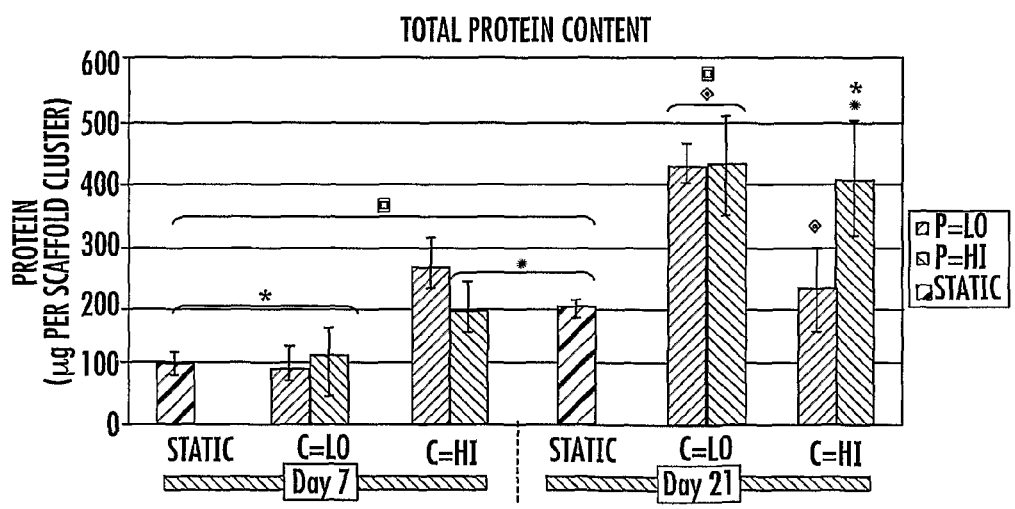
FIG. 14 illustrates total protein content assay results in the bioreactor study described in Example 2.

The dynamic mechanical stimulus of the culture chambers appeared to prompt extra-cellular matrix (ECM) production as indicated by the total protein content results (FIG. 14). The culture chamber design was intended to mimic in vivo conditions and in effect cause the cells to product bone-like ECM. Total protein content was clearly improved by day 21 as compared to the static culture protocol. As occurs in vivo, the active loading within the culture chamber can force a cell to lay down new ECM to surround itself with new "bone" and afford the cell's long-term anchorage to the scaffold for continued survival.

Figure 15:
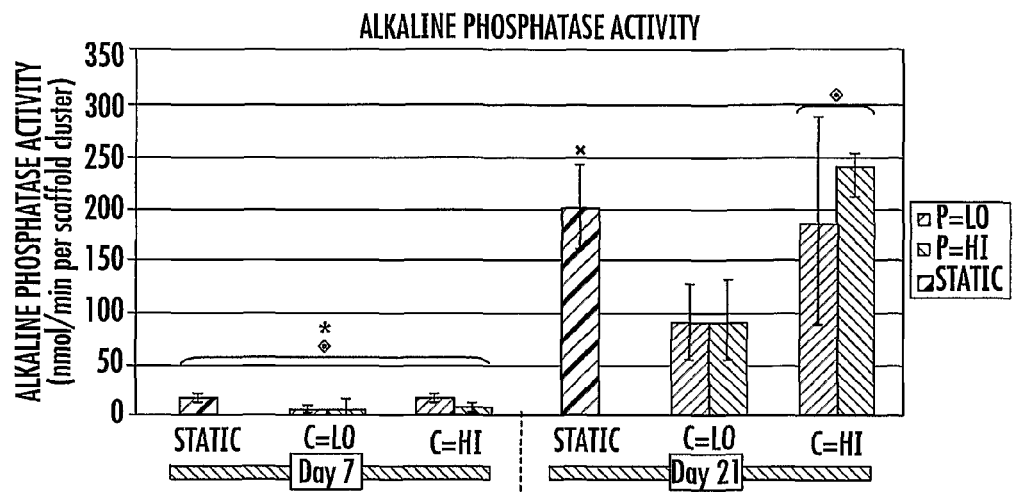
FIG. 15 illustrates alkaline phosphatase activity in the bioreactor study described in Example 2.
Figure 16:
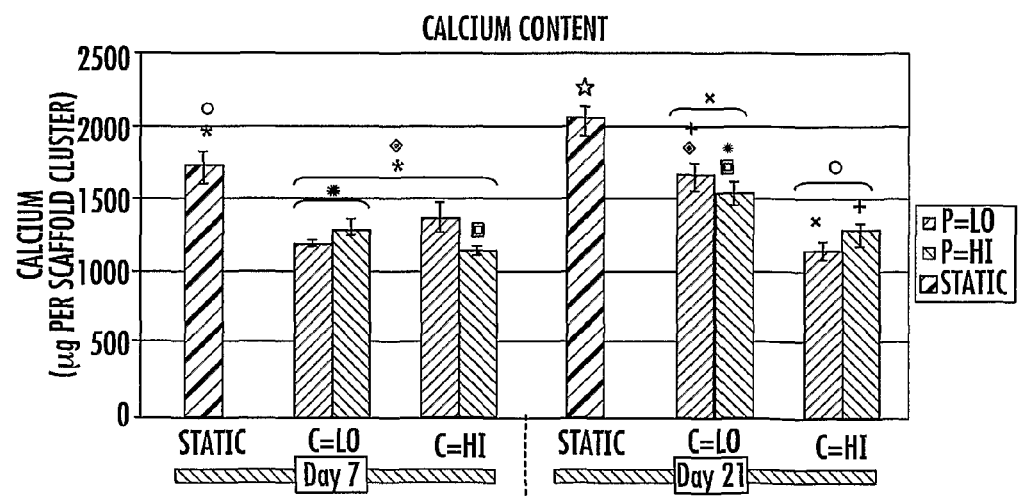
FIG. 16 illustrates calcium content assayed in the bioreactor study described in Example 2.
Figure 17:
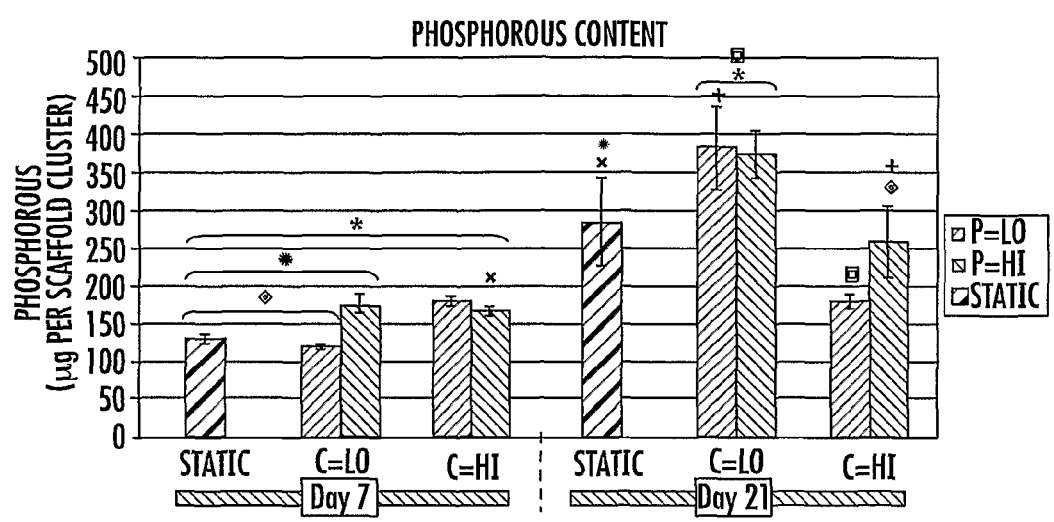
FIG. 17 illustrates phosphorous content assayed in the bioreactor study described in Example 2.

ALP activity has often been used to indicate cell differentiation toward the osteogenic lineage. In this case, both the static culture and high compression protocols indicated increased levels of cell differentiation through the statistical increase in ALP activity from day 7 to day 21 (FIG. 15).

Calcium and phosphorous contents (FIGS. 16 and 17) appeared to uniquely vary over time as well as in respect to the static culture regimens. Studies that did not undergo hydrostatic compression demonstrated a statically significant increase in both calcium and phosphorous content from day 7 to day 21. Studies including hydrostatic compression showed no statistical change and even slight numerical reduction in calcium and phosphorous content over time. It is believed that the effect of compression may have broken up the more brittle mineralized portion of the ECM, allowing fragments to be swept out of the chamber by the ensuing perfusion flow, thereby reducing the endpoint level of calcium and phosphorous within the three dimensional construct.

These and other modifications and variations to the present disclosure can be practiced by those of ordinary skill in the art, without departing from the spirit and scope of the present disclosure, which is more particularly set forth in the appended claims. In addition, it should be understood that aspects of the various embodiments can be interchanged both in whole or in part. Furthermore, those of ordinary skill in the art will appreciate that the foregoing description is by way of example only and is not intended to limit the disclosure so further described in such appended claims.

What is claimed is:

1. A 3D bioreactor system comprising:
   a first module independently defining a first culture chamber therein, a first inlet, and a first outlet, the first inlet and first outlet providing a passage for a first fluid flow through said first culture chamber, said first culture chamber being formed of a material to discourage cellular attachment to said first culture chamber;
   a second module independently defining a second culture chamber therein, a second inlet, and a second outlet, the second inlet and second outlet providing a second fluid flow through said second culture chamber, said second culture chamber being formed of a material to discourage cellular attachment to said second culture chamber;
   a semi-permeable membrane locatable between said first culture chamber of said first module and said second culture chamber of said second module, wherein said semi-permeable membrane has a porosity to allow passage of cellular expression products through said semi-permeable membrane and to prevent passage of cells through said semi-permeable membrane, said semi-permeable membrane being formed of a material to discourage cellular attachment to said semi-permeable membrane; and
   a cellular anchorage locatable in said first culture chamber.

2. The 3D bioreactor system of claim 1, wherein said cellular anchorage comprises multiple discrete scaffolds.

3. The 3D bioreactor system of claim 2, further comprising a retaining mesh, wherein said retaining mesh is locatable within said first culture chamber to prevent said multiple discrete scaffolds from passage through said first outlet.

4. A 3D bioreactor system comprising:
   a first module independently defining a first culture chamber therein,
   a first inlet, and a first outlet, the first inlet and first outlet providing a passage for a first fluid flow through said first culture chamber;
   a second module independently defining a second culture chamber therein,
   a second inlet, and a second outlet, the second inlet and second outlet providing a passage for a second fluid flow through said second culture chamber;
   a semi-permeable membrane locatable between said first culture chamber of said first module and said second culture chamber of said second module, wherein said semi-permeable membrane has a porosity to allow passage of cellular expression products through said semi-permeable membrane and to prevent passage of cells through said semi-permeable membrane; and
   a cellular anchorage, said cellular anchorage being locatable within said first culture chamber at a distance from said semi-permeable membrane,
   wherein said first culture chamber, said second culture chamber, and said semi-permeable membrane are formed of a material to discourage cellular attachment to said first and second culture chamber and said semi-permeable membrane.

5. The 3D bioreactor system of claim 4, wherein said cellular anchorage comprises multiple discrete scaffolds.

6. The 3D bioreactor system of claim 5, further comprising a retaining mesh, wherein said retaining mesh is locatable within said first culture chamber to prevent said multiple discrete scaffolds from passage through said first outlet.

7. The 3D bioreactor system of claim 4, wherein said cellular anchorage comprises a continuous scaffold.

8. The 3D bioreactor system of claim 4, further comprising a pressure module locatable adjacent said first culture chamber.

9. The 3D bioreactor system of claim 4, further comprising a third module independently defining a third culture chamber therein, a third inlet, and a third outlet, the third inlet and third outlet providing a passage for a third fluid flow through said third culture chamber; and a semi-permeable membrane locatable between said first culture chamber of said first module and said third culture chamber of said third module, wherein said semi-permeable membrane has a porosity to allow passage of cellular expression products through said semi-permeable membrane and to prevent passage of cells through said semipermeable membrane.

10. A method for culturing cells comprising:
providing a first cell type to a first culture chamber of a first module, the first module independently defining the first culture chamber therein, a first inlet, and a first outlet, the first inlet and first outlet allowing a first fluid flow through said first culture chamber;
developing a three dimensional cellular construct within said first culture chamber, said three dimensional cellular construct comprising said first cell type;
providing a second cell type to a second culture chamber of a second module, the second module independently defining the second culture chamber therein, a second inlet, and a second outlet, the second inlet and second outlet allowing a second fluid flow through said second culture chamber;
locating a cellular anchorage within said first culture chamber;
maintaining said first cell type and said second cell type in a physically isolated state from one another; and
allowing biochemical communication between said first said cell type and said second cell type via a semi-permeable membrane locatable between said first culture chamber and said second culture chamber, wherein said first culture chamber and said second culture chamber are formed of a material to discourage cellular attachment to said first and second culture chambers.

11. The method according to claim 10, wherein said first cell type is an undifferentiated cell type, said method further comprising triggering differentiation of said undifferentiated cell type.

12. The method according to claim 10, further comprising seeding said first cell type onto said cellular anchorage.

13. The method according to claim 10, further comprising subjecting said first cell type to at least one mechanical stimulus.

14. The method according to claim 13, wherein said at least one mechanical stimulus comprises hydrostatic pressure.

15. The method according to claim 13, wherein said at least one mechanical stimulus comprises shear stress.

16. The method according to claim 10, further comprising providing a third cell type and allowing biochemical communication between said third cell type and said first cell type.

17. A 3D bioreactor system comprising:
a first module independently defining a first culture chamber therein, a first inlet, and a first outlet, the first inlet and first outlet providing a first fluid flow through said first culture chamber;
a second module independently defining a second culture chamber therein,
a second outlet for providing a second fluid flow through said second culture chamber,
a semi-permeable membrane locatable between said first culture chamber of said first module and said second culture chamber of said second module, wherein said semi-permeable membrane has a porosity to allow passage of cellular expression products through said semi-permeable membrane and to prevent passage of cells through said semi-permeable membrane, said semi-permeable membrane being formed of a material to discourage cellular attachment to said semi-permeable membrane; and
a cellular anchorage, said anchorage being locatable within said first culture chamber at a distance from said semi-permeable membrane.

18. The 3D bioreactor system of claim 17, further comprising a third module independently defining a third culture chamber therein, a third inlet, and a third outlet, the third inlet and third outlet providing a third fluid flow through said third culture chamber, wherein said first culture chamber and said third culture chamber are in biochemical communication with one another.

19. The 3D bioreactor system of claim 17, further comprising a third module independently defining a third culture chamber therein, a third inlet, and a third outlet, the third inlet and third outlet providing a passage for a third fluid flow through said third culture chamber; and a semi-permeable membrane locatable between said first culture chamber and said third culture chamber, wherein said semi-permeable membrane has a porosity to allow passage of cellular expression products through said semi-permeable membrane and to prevent passage of cells through said semipermeable membrane.

20. A method for culturing cells comprising:
providing a first cell type to a first culture chamber of a first module, the first module independently defining the first culture chamber therein, a first inlet, and a first outlet, the first inlet and first outlet allowing a first fluid flow through said first culture chamber;
developing a three dimensional cellular construct within said first culture chamber, said three dimensional cellular construct comprising said first cell type;
providing a second cell type to a second culture chamber of a second module, the second module independently defining the second culture chamber therein, a second inlet, and a second outlet, the second inlet and second outlet allowing a second fluid flow through said second culture chamber;
maintaining said first cell type and said second cell type in a physically isolated state from one another; and allowing biochemical communication between said first said cell type and said second cell type; and
allowing biochemical communication between said first said cell type and said second cell type via a semi-permeable membrane locatable between said first culture chamber and second culture chamber, wherein said first culture chamber and said second culture chamber are formed of a material to discourage cellular attachment to said first and second culture chamber.

21. A 3D bioreactor system comprising:
a first module independently defining a first culture chamber therein, a first inlet, and a first outlet, the first inlet and first outlet providing a passage for a first fluid flow through said first culture chamber, said first culture chamber being formed of a material to discourage cellular attachment to said first culture chamber;
a second module independently defining a second culture chamber therein, a second inlet, and a second outlet, the second inlet and the second outlet providing a second fluid flow through said second culture chamber, said second culture chamber being formed of a material to discourage cellular attachment to said second culture chamber;

a cellular anchorage, said cellular anchorage locatable in said first chamber, in said second chamber, or bother; and a membrane locatable between said first culture chamber and said second culture chamber, wherein said separator has an orientation that is substantially parallel to the central axes of the first and second inlets and first and second outlets.

22. The bioreactor system of claim 21, wherein the separator is a semi-permeable membrane.

23. The 3D bioreactor system of claim 21, wherein said cellular anchorage comprises a continuous scaffold.

24. The 3D bioreactor system of claim 22, wherein said semipermeable membrane is a polycarbonate membrane.

25. The 3D bioreactor system of claim 21, further comprising a pressure module locatable adjacent said first culture chamber.

26. The 3D bioreactor system of claim 21, further comprising a third module independently defining a third culture chamber therein, a third inlet, and a third outlet providing a passage for a third fluid flow through said third culture chamber.

27. The 3D bioreactor system of any of claim 1, 4, or 17, wherein the second culture chamber is located vertically relative to the first culture chamber.

28. The 3D bioreactor system of any of claim 1, 4, or 17, wherein the first and second culture chambers are uncoated.

29. The 3D bioreactor system of any of claim 1, 4, or 17, wherein the first module and second module are of monolithic construction.

* * * * *